(12) United States Patent
Field

(10) Patent No.: US 9,155,653 B2
(45) Date of Patent: Oct. 13, 2015

(54) PRESSURE-DRIVEN MEMBRANE VALVE FOR PRESSURE CONTROL SYSTEM

(75) Inventor: Leslie A Field, Portola Valley, CA (US)

(73) Assignee: Alcon Research, Ltd., Fort Worth, TX (US)

(*) Notice: Subject to any disclaimer, the term of this patent is extended or adjusted under 35 U.S.C. 154(b) by 524 days.

(21) Appl. No.: 13/372,849

(22) Filed: Feb. 14, 2012

(65) Prior Publication Data
US 2013/0211311 A1    Aug. 15, 2013

(51) Int. Cl.
A61F 9/007    (2006.01)

(52) U.S. Cl.
CPC ..... *A61F 9/00781* (2013.01); *A61F 2250/0018* (2013.01); *Y10T 137/7895* (2015.04)

(58) Field of Classification Search
USPC ............................................................ 604/8
See application file for complete search history.

(56) References Cited

U.S. PATENT DOCUMENTS

| | | |
|---|---|---|
| 4,089,329 A | 5/1978 | Couvillon et al. |
| 4,206,762 A | 6/1980 | Cosman |
| 4,457,757 A | 7/1984 | Molteno |
| 4,656,827 A | 4/1987 | Puillet |
| 4,750,901 A | 6/1988 | Molteno |
| 4,922,913 A | 5/1990 | Waters et al. |
| 5,005,577 A | 4/1991 | Frenkel |
| 5,178,604 A | 1/1993 | Baerveldt |
| 5,179,953 A | 1/1993 | Kursar |
| 5,397,300 A | 3/1995 | Baerveldt |
| 5,437,627 A * | 8/1995 | Lecuyer ............................. 604/9 |
| 5,476,445 A | 12/1995 | Baerveldt |
| 5,558,629 A | 9/1996 | Baerveldt |
| 5,573,646 A | 11/1996 | Saito et al. |
| 5,626,558 A | 5/1997 | Suson |
| 5,681,275 A | 10/1997 | Ahmed |
| 5,910,110 A | 6/1999 | Bastable |
| 6,007,511 A | 12/1999 | Prywes |
| 6,048,328 A | 4/2000 | Haller et al. |
| 6,090,062 A * | 7/2000 | Sood et al. ....................... 604/9 |

(Continued)

FOREIGN PATENT DOCUMENTS

| | | |
|---|---|---|
| DE | 4438201 | 5/1996 |
| EP | 2427097 | 3/2012 |

(Continued)

OTHER PUBLICATIONS

International Searching Authority, International Search Report of the International Searching Authority, PCT/US2010/047612, Dec. 21, 2010, 7 pages.

(Continued)

*Primary Examiner* — Leslie Deak
*Assistant Examiner* — Kai Weng
(74) *Attorney, Agent, or Firm* — Haynes and Boone, LLP

(57) ABSTRACT

A control valve for a fluidic system is disclosed. The control valve comprises a housing and a flow control membrane is disclosed. The flow control membrane is anchored within the housing to form a reference chamber on a first side of the membrane and a fluid flow channel on a second opposing side of the membrane. The fluid flow channel selectively opens and closes to permit fluid to flow from the inlet to the outlet, and the membrane is configured to control flow through the channel from the inlet to the outlet by deflecting in response to pressure differentials of the reference chamber pressure and the fluid flow channel pressure acting across the membrane.

26 Claims, 5 Drawing Sheets

(56) References Cited

U.S. PATENT DOCUMENTS

| | | | |
|---|---|---|---|
| 6,447,449 B1 | 9/2002 | Fleischman et al. | |
| 6,468,283 B1 | 10/2002 | Richter et al. | |
| 6,544,208 B2* | 4/2003 | Ethier et al. | 604/8 |
| 6,579,235 B1 | 6/2003 | Abita et al. | |
| 6,589,198 B1 | 7/2003 | Soltanpour et al. | |
| 6,682,500 B2 | 1/2004 | Soltanpour et al. | |
| 6,712,764 B2 | 3/2004 | Jeffries et al. | |
| 6,749,568 B2 | 6/2004 | Fleischman et al. | |
| 6,939,299 B1 | 9/2005 | Petersen et al. | |
| 7,137,952 B2 | 11/2006 | Leonardi et al. | |
| 7,169,106 B2 | 1/2007 | Fleischman et al. | |
| 7,252,006 B2 | 8/2007 | Tai et al. | |
| 7,354,416 B2 | 4/2008 | Quiroz-Mercado et al. | |
| 7,409,863 B2 | 8/2008 | Bateman et al. | |
| 7,612,328 B2 | 11/2009 | Kaiser | |
| 7,824,699 B2 | 11/2010 | Ralph et al. | |
| 7,882,612 B2* | 2/2011 | Dehe et al. | 29/594 |
| 8,182,435 B2 | 5/2012 | Dacquay et al. | |
| 8,257,295 B2 | 9/2012 | Rickard et al. | |
| 2001/0000527 A1 | 4/2001 | Yaron et al. | |
| 2002/0019607 A1 | 2/2002 | Bui | |
| 2002/0049374 A1 | 4/2002 | Abrea | |
| 2002/0087111 A1 | 7/2002 | Ethier et al. | |
| 2002/0099359 A1 | 7/2002 | Santini, Jr. et al. | |
| 2002/0143284 A1 | 10/2002 | Tu et al. | |
| 2002/0193674 A1 | 12/2002 | Fleischman et al. | |
| 2003/0078487 A1 | 4/2003 | Jeffries et al. | |
| 2003/0225318 A1 | 12/2003 | Montegrande et al. | |
| 2004/0013702 A1 | 1/2004 | Glover | |
| 2004/0059248 A1 | 3/2004 | Messner et al. | |
| 2004/0073137 A1 | 4/2004 | Lloyd et al. | |
| 2004/0111050 A1 | 6/2004 | Smedley et al. | |
| 2004/0116794 A1 | 6/2004 | Fink et al. | |
| 2004/0186367 A1 | 9/2004 | Fresco | |
| 2004/0254438 A1 | 12/2004 | Chuck et al. | |
| 2004/0254517 A1 | 12/2004 | Quiroz-Mercado et al. | |
| 2004/0254521 A1 | 12/2004 | Simon | |
| 2005/0049578 A1 | 3/2005 | Tu et al. | |
| 2005/0159660 A1 | 7/2005 | Montegrande et al. | |
| 2005/0271704 A1 | 12/2005 | Tu et al. | |
| 2005/0273033 A1 | 12/2005 | Grahn et al. | |
| 2006/0131350 A1 | 6/2006 | Schechter et al. | |
| 2007/0019156 A1 | 1/2007 | Fink | |
| 2007/0032757 A1 | 2/2007 | Medow et al. | |
| 2007/0106199 A1 | 5/2007 | Krivoy et al. | |
| 2007/0109117 A1 | 5/2007 | Heitzmann et al. | |
| 2007/0123767 A1 | 5/2007 | Montegrande et al. | |
| 2007/0129623 A1 | 6/2007 | Fleischmann et al. | |
| 2007/0212397 A1 | 9/2007 | Roth | |
| 2008/0015421 A1 | 1/2008 | Penner | |
| 2008/0077127 A1 | 3/2008 | Gao et al. | |
| 2008/0125691 A1 | 5/2008 | Yaron et al. | |
| 2008/0129486 A1 | 6/2008 | Jeckelmann et al. | |
| 2008/0215062 A1 | 9/2008 | Bowen et al. | |
| 2008/0228127 A1 | 9/2008 | Burns et al. | |
| 2009/0036819 A1 | 2/2009 | Tu et al. | |
| 2009/0069648 A1 | 3/2009 | Irazqui et al. | |
| 2009/0076367 A1 | 3/2009 | Sit et al. | |
| 2009/0143713 A1 | 6/2009 | Van Dam et al. | |
| 2009/0227933 A1 | 9/2009 | Karageozian | |
| 2009/0275924 A1 | 11/2009 | Lattanzio et al. | |
| 2009/0312742 A1 | 12/2009 | Pang et al. | |
| 2010/0010416 A1 | 1/2010 | Juan, Jr. et al. | |
| 2010/0042209 A1 | 2/2010 | Guarnieri | |
| 2010/0121348 A1 | 5/2010 | Van Der Burg et al. | |
| 2010/0234717 A1 | 9/2010 | Wismer | |
| 2010/0253167 A1 | 10/2010 | Charnley et al. | |
| 2011/0046536 A1 | 2/2011 | Stegmann et al. | |
| 2011/0071454 A1 | 3/2011 | Santos et al. | |
| 2011/0071456 A1 | 3/2011 | Rickard | |
| 2011/0113889 A1* | 5/2011 | Funken et al. | 73/715 |
| 2011/0192473 A1* | 8/2011 | Meinig et al. | 137/488 |
| 2011/0248671 A1 | 10/2011 | Santos et al. | |

FOREIGN PATENT DOCUMENTS

| | | |
|---|---|---|
| WO | WO 93/03665 | 3/1993 |
| WO | WO 98/03665 | 1/1998 |
| WO | WO 99/38470 A2 | 8/1999 |
| WO | WO 99/38470 A3 | 10/1999 |
| WO | WO 01/94784 | 12/2001 |
| WO | WO 03/001991 | 1/2003 |
| WO | WO 03/102632 | 12/2003 |
| WO | WO 2007/127305 A2 | 11/2007 |
| WO | WO 2007/136993 | 11/2007 |
| WO | WO 2008/061043 | 5/2008 |
| WO | WO 2008/061043 A2 | 5/2008 |
| WO | WO 2009/026499 | 2/2009 |
| WO | WO 2009/049686 | 4/2009 |
| WO | WO 2009/081031 | 7/2009 |
| WO | WO 2009/081031 A3 | 9/2009 |
| WO | WO 2010/129446 | 11/2010 |
| WO | WO 2011/034727 A1 | 3/2011 |
| WO | WO 2011/034738 A1 | 3/2011 |
| WO | WO 2011/034740 A1 | 3/2011 |
| WO | WO 2011/034742 A2 | 3/2011 |
| WO | WO 2011/035218 A1 | 3/2011 |
| WO | WO 2011/034742 A3 | 5/2011 |

OTHER PUBLICATIONS

International Searching Authority, Written Opinion of the International Searching Authority, PCT/US2010/047612, Dec. 21, 2010, 10 pages.

Nisar A., Afzulpurkar Nitin, Mahaisavariya Banchong, and Tuantranont Adisorn; "MEMS-Based Micropumps in Drug Delivery and Biomedical Applications"; ScienceDirect; Sensors and Actuators B 130 (2008) pp. 917-942.

Neagu Cristina R.; "A Medical Microactuator Based on an Electrochemical Principle"; Thesis at the Twente University,the Netherlands, Enschede; Aug. 28, 1998; pp. 1-162.

Saloomeh Saati MD., Ronalee Lo PhD, Po-Ying Li PhD, Ellis Meng PhD, Rohit Varma MD MPH, and Mark S. Humayun MD PhD; "Mini Drug Pump for Ophthalmic Use"; Trans Am Ophthalmol Soc 2009; 107; pp. 60-71.

Erik Stemme and Goran Stemme; "A Valveless Diffuser/Nozzle-Based Fluid Pump"; ScienceDirect; Sensors and Actuators A, 39 (1993); pp. 159-167.

Byunghoon Bae, Hongseok Kee, Seonho Kim, Yeon Lee, Taeseok Sim, Yongkweon Him and Kyihwan Park; "In Vitro Experiment of the Pressure Regulating Valve for a Glaucoma Impact"; Journal of Micromechanics and Microengineering, 13 (2003); pp. 613-619.

Eggers, T., et al, "Wireless Intra-Ocular Pressure Monitoring System Integrated Into an Artificial Lens," 1st Annual Int'l IEEE-EMBS Special Topic Conference on Microtechnologies in Medicine & Biology, Oct. 12-14, 2000, pp. 466-469, Lyon, France.

Greene, M.E. and Gilman, B.G., "Intraocular Pressure Measurement With Instrumented Contact Lenses," Investigative Ophthalmology & Visual Science (IVOS), Apr. 1974, pp. 299-302, vol. 13, No. 4, IVOS.

Hjortdal, Jesper and Jensen, Peter, "In Vitro Measurement of Corneal Strain, Thickness, and Curvature Using Digital Image Processing," Acta Ophthalmologica Scandinavica, 1995, pp. 5-11, vol. 73, Denmark.

International Searching Authority, Search Report and Written Opinion of the International Searching Authority, PCT/US2010/033329, Jul. 13, 2010, 14 pages.

International Searching Authority, Search Report and Written Opinion of the International Searching Authority, PCT/US2010/047429, Nov. 1, 2010, 15 pages.

International Searching Authority, Search Report and Written Opinion of the International Searching Authority, PCT/US2010/047600, Dec. 14, 2010, 13 pages.

International Searching Authority, Search Report and Written Opinion of the International Searching Authority, PCT/US2010/049424, Nov. 26, 2010, 15 pages.

International Searching Authority, Search Report of the International Searching Authority, PCT/US2011/036742, Aug. 17, 2011, 2 pages.

Lam, Andrew K.C. and Douthwaite, William A., "The Effect of an Artificially Intraocular Pressure on the Central Corneal Curvature,"

(56) References Cited

OTHER PUBLICATIONS

Ophthalmic and Physiological Optics, 1997, pp. 18-24, vol. 17, No. 1, Elsevier Science, Ltd., Great Britain.

Leonardi, Matteo, et al., "A Soft Contact Lens With a Mems Strain Gage Embedded for Intraocular Pressure Monitoring," In Proc. 12th Int'l Conference on Solid State Sensors, Actuators and Microsystems, Jun. 8-12, 2003, pp. 1043-1046, vol. 2, Boston, MA.

Leonardi, Matteo, et al., "First Steps Toward Noninvasive Intraocular Pressure Monitoring with a Sensing Contact Lens," Investigative Ophthalmology & Visual Science (IVOS), 2004, pp. 3113-3117, vol. 45, No. 9, IVOS.

McLaren, Jay W., et al, "Continuous Measurement of Intraocular Pressure in Rabbits by Telemetry," Investigative Ophthalmology & Visual Science (IVOS), May 1996, pp. 966-975, vol. 37, No. 6, IVOS.

Mokwa, Wilfried, et al, "Micro-Transponder Systems for Medical Applications," IEEE Transactions on Instrumentation and Measurement, Dec. 2001, pp. 1551-1555, vol. 50, No. 6, IEEE, Germany.

Puers, Robert, "Linking Sensors with Telemetry: Impact on the System Design," In Proc. 8th Int'l Conference of Solid State Sensors, Actuators, Eurosens, Jun. 25-29, 1995, pp. 169-174, Stockholm, Sweden.

Schnakenberg, U., et al, "Initial Investigations on Systems for Measuring Intraocular Pressure," Sensors and Actuators, 2000, p. 287-291, vol. 85, Elsevier Science B.V., Germany.

Stangel, Karsten, et al, "A Programmable Intraocular CMOS Pressure Sensor System Implant," IEEE Journal of Solid-State Circuits, Jul. 2001, pp. 1094-1100, vol. 36, No. 7, IEEE, Germany.

Ullerich, Stella, et al, "Micro Coils for an Advanced System for Measuring Intraocular Pressure," 1st Annual Int'l IEEE-EMBS Special Topic Conference on Microtechnologies in Medicine & Biology, Oct. 12-14, 2000, pp. 470-474, Lyon, France.

Van Schuylenbergh, K., et al, "An Implantable Telemetric Tonometer for Direct Intraocular Pressure Measurements," 1st European Conference on Biomedical Engineering, Feb. 1991, pp. 194-195, vol. 17, No. 20, Nice, France.

Walter, Peter; "Intraocular Pressure Sensor: Where Are We—Where Will We Go?" Journal Graefe's Archive for Clinical and Experimental Ophthalmology; Publisher Springer Berline/Heidelberg; ISSN 0721-832X (Print) 1435-702X (Online); Issue vol. 240, No. 5/May 2002 DOI 10.1007/s00417-002-0474-y; pp. 335-336; Subject Collection Medicine.

International Searching Authority, Written Opinion of the International Searching Authority, PCT/US2010/047605, Dec. 16, 2010, 9 pages.

International Search Report and Written Opinion issued for PCT/US2013/026066, dated Apr. 17, 2013, 13 pages.

\* cited by examiner

PRESSURE-DRIVEN MEMBRANE VALVE FOR PRESSURE CONTROL SYSTEM

BACKGROUND

The present disclosure relates generally to membrane valves and associated systems and methods for use in ophthalmic treatments. In some instances, embodiments of the present disclosure are configured to be part of an IOP control system.

Glaucoma, a group of eye diseases affecting the retina and optic nerve, is one of the leading causes of blindness worldwide. Most forms of glaucoma result when the intraocular pressure (IOP) increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

The eye's ciliary body continuously produces aqueous humor, the clear fluid that fills the anterior segment of the eye (the space between the cornea and lens). The aqueous humor flows out of the anterior chamber (the space between the cornea and iris) through the trabecular meshwork and the uveoscleral pathways, both of which contribute to the aqueous drainage system. The delicate balance between the production and drainage of aqueous humor determines the eye's IOP.

FIG. 1 is a diagram of the front portion of an eye that helps to explain the processes of glaucoma. In FIG. 1, representations of the lens 110, cornea 120, iris 130, ciliary body 140, trabecular meshwork 150, and Schlemm's canal 160 are pictured. Anatomically, the anterior segment of the eye includes the structures that cause elevated IOP which may lead to glaucoma. Aqueous fluid is produced by the ciliary body 140 that lies beneath the iris 130 and adjacent to the lens 110 in the anterior segment of the eye. This aqueous humor washes over the lens 110 and iris 130 and flows to the drainage system located in the angle of the anterior chamber. The angle of the anterior chamber, which extends circumferentially around the eye, contains structures that allow the aqueous humor to drain. The trabecular meshwork 150 is commonly implicated in glaucoma. The trabecular meshwork 150 extends circumferentially around the anterior chamber. The trabecular meshwork 150 seems to act as a filter, limiting the outflow of aqueous humor and providing a back pressure that directly relates to IOP. Schlemm's canal 160 is located beyond the trabecular meshwork 150. Schlemm's canal 160 is fluidically coupled to collector channels (not shown) allowing aqueous humor to flow out of the anterior chamber. The two arrows in the anterior segment of FIG. 1 show the flow of aqueous humor from the ciliary bodies 140, over the lens 110, over the iris 130, through the trabecular meshwork 150, and into Schlemm's canal 160 and its collector channels.

One method of treating glaucoma includes implanting a drainage device in a patient's eye. The drainage device allows fluid to flow from the interior chamber of the eye to a drainage site, relieving pressure in the eye and thus lowering IOP. These devices are generally passive devices and do not provide a smart, interactive control of the amount of flow through the drainage tube. In addition, fluid filled blebs frequently develop at the drainage site. The development and over-pressurization of the bleb typically induces fibrosis, which leads to increased flow resistance and it is generally the case that this resistance increases overtime. This development and progression of fibrosis reduces or eliminates flow from the anterior chamber, eliminating the capacity of the drainage device to affect IOP. Current drainage devices often employ passive check valves that operate by comparing the IOP and the pressure at the drainage site. Such valves have no mechanism for controlling over-pressurization within the bleb, which may increase to unacceptable levels with over-drainage of aqueous humor into the bleb.

Accordingly, there exists a need for an IOP control system or implant that protects against under-drainage while simultaneously guarding against over-drainage, and consequently minimizes bleb formation and subsequent fibrotic changes. Providing actively responsive valves in the IOP control system that function even in the absence of an energy supply may reduce bleb formation and subsequent fibrotic changes, and thus significantly increase the functional life of the IOP control system. The system and methods disclosed herein overcome one or more of the deficiencies of the prior art.

SUMMARY

In one exemplary aspect, the present disclosure is directed to a control valve for a fluidic system. The control valve includes a housing and a flow control membrane. The housing comprises a fluid inlet and a fluid outlet. The flow control membrane is anchored within the housing to a reference chamber having a reference chamber pressure on a first side of the flow control membrane and a fluid flow channel on a second opposing side of the membrane. The fluid flow channel selectively opens and closes to permit fluid to flow from the fluid inlet to the fluid outlet, and the flow control membrane is configured to control flow through the fluid flow channel from the fluid inlet to the fluid outlet by deflecting in response to pressure differentials of the reference chamber pressure and the fluid flow channel pressure acting on the opposing sides of the flow control membrane.

In another exemplary aspect, the present disclosure is directed to an IOP control system for implantation in an eye of a patient that comprises a drainage tube and a pressure-driven membrane valve. The drainage tube is configured to convey aqueous humor from an anterior chamber of the eye, and the valve is in fluid communication with the drainage tube. The pressure-driven membrane valve is actuatable in response to pressure differentials and is configured to control flow rates of the aqueous humor along the drainage tube by deflecting in response to pressure differentials between the anterior chamber of the eye and an atmospheric pressure acting on the pressure-driven membrane valve.

In some instances, the pressure-driven membrane valve comprises a housing, a valve seat, and a flow control membrane. The housing includes a fluid inlet and a fluid outlet, and the valve seat is positioned within the housing between the fluid inlet and the fluid outlet. The flow control membrane is anchored within the housing to form a reference chamber on a first side of the flow control membrane and a fluid flow channel on a second side of the membrane. The fluid flow channel selectively opens and closes to permit fluid to flow from the fluid inlet to the fluid outlet, and the flow control membrane is configured to control flow through the fluid flow channel from the fluid inlet to the fluid outlet by deflecting in response to pressure differentials acting on the sides of the flow control membrane.

In another exemplary aspect, the present disclosure is directed to a pressure-driven IOP control valve for implantation in an eye of a patient that comprises a housing and a flow control membrane. The housing includes a fluid inlet and a fluid outlet. The flow control membrane is anchored within the housing to form a reference chamber on a first side of the flow control membrane and a fluid flow channel on a second side of the membrane, wherein the fluid flow channel fluidly connects the fluid inlet to the fluid outlet. The flow control membrane includes at least one corrugation and is configured to control flow through the fluid flow channel from the fluid inlet to the fluid outlet by deflecting in response to pressure differentials acting on the sides of the flow control membrane.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
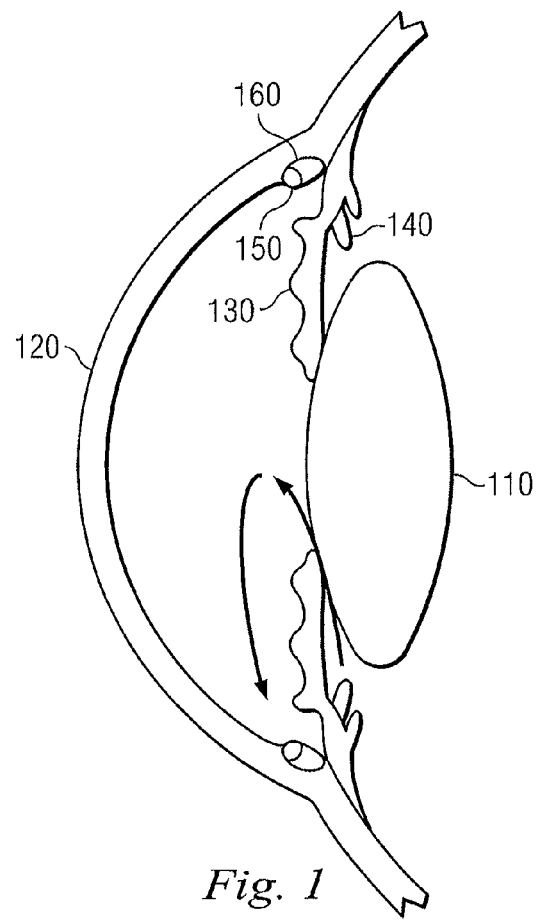
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

Figure 2:
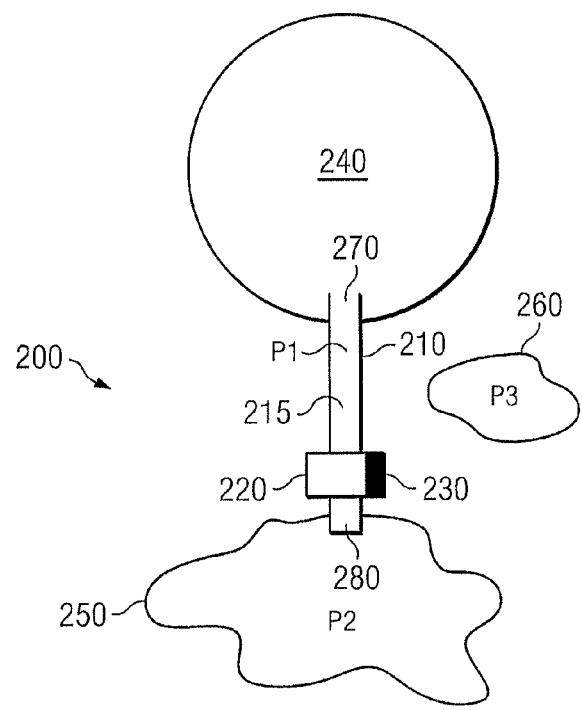
FIG. 2 is a schematic diagram of an exemplary IOP control system according to one embodiment of the present disclosure.

FIG. 2 is a diagram of an exemplary IOP control system 200, including a drainage tube 210, a valve system 220, and a divider 230. The IOP control system 200 is positioned in the eye with one end 270 of the drainage tube 210 located in the anterior chamber 240 and the opposite end 280 located outside the anterior chamber 240 in a drainage site 250.

In some examples, the valve system 220 may be formed as a part of or utilized in a valve system such as those disclosed in related application Ser. No. 13/315,329, titled "Active Drainage Systems with Pressure-Driven Valves and Electronically-Driven Pump," incorporated herein by reference. The pressure-driven membrane valves disclosed herein may form the downstream valves of the valve system in the incorporated application, titled "Active Drainage Systems with Pressure-Driven Valves and Electronically-Driven Pump."

In some embodiments, the IOP control system 200 may be positioned within the eye in the subconjunctival pocket between the conjunctiva and the sclera with the anterior border of the valve system 220 positioned approximately 8 to 10 mm posterior to the limbus (the border between the cornea and the sclera). The IOP control system 200 may be held in place within the eye via anchoring structures, the angle of implantation and surrounding anatomy, or by a spring force or other mechanisms that stabilize the IOP control system 200.

In the embodiment pictured in FIG. 2, three areas of pressure interact with the IOP sensor system 200: P1, P2, and P3. Pressure area P1 reflects the pressure of the anterior chamber 240, pressure area P2 reflects the pressure of the drainage site 250 in the subconjunctival space or at least partially in the socket of the eye (and may reflect bleb pressure), and pressure area P3 reflects a reference pressure located remotely from P1 and P2 in a (relatively) dry location 260 (effectively reflecting atmospheric pressure). In some embodiments, pressure area P1 reflects the pressure located in a lumen or tube that is in fluidic communication with the anterior chamber 240.

The IOP control system 200 responds to the pressure differentials between P1, P2, and P3 to control the valve system 220 and thereby control the flow rate of aqueous humor through drainage tube 210. More specifically, the various pressure differentials across pressure areas P1, P2, and P3 (P1-P2, P1-P3, P2-P3) drive the valve system 220 and dictate the flow rate of aqueous humor through the drainage tube 210 without requiring external power at the valve system 220.

The drainage tube 210 drains aqueous humor from the anterior chamber 240 of the eye. The valve system 220 controls the flow of aqueous humor through a lumen 215 of the tube 210. In the embodiment shown, the pressure area P1 reflects the pressure in the lumen 215 upstream from the valve system 220 and downstream from the anterior chamber 240. The expected discrepancy between the true anterior chamber pressure and that reflected by area P1 when located in a tube downstream of the anterior chamber 240 (even when located between the sclera and the conjunctiva) is very minimal. For example, Poiseuille's law for pipe flow predicts a pressure drop of 0.01 mmHg across a 5-millimeter long tube with a 0.300 millimeter inner diameter for a flow rate of 3 microliters per minute of water. Therefore, because there is almost no pressure difference between the anterior chamber 240 and the interior of the tube 210 that is in fluid contact with the anterior chamber 240, pressure area P1 effectively reflects the pressure of the anterior chamber 240.

In some embodiments, a divider 230 separates pressure areas P1 and P2 from pressure area P3. Pressure area P2 reflects the pressure at a drainage site 250. As such, pressure area P2 may be located in a pocket, such as a bleb, that generally contains aqueous humor or in communication with such a pocket, via a tube, for example, and is in a wet location. Pressure area P3 is physically separated from both pressure area P1 and pressure area P2 by divider 230. Divider 230 is a physical structure that separates and isolates the pressure area P1 and the wet drainage site 250 of pressure area P2 from the dry location 260 of pressure area P3. In some embodiments, the divider 230 includes the physical components of the valve system 220, such as parts of a housing. Note that the divider 230 may take many forms, such as, but not limited to, a tube extending pressure area P3 to a remote site or a pocket away from and fluidly independent of the drainage site.

In some embodiments of the present disclosure, the atmospheric pressure area P3 reflects the pressure in an area in close proximity to the eye, and in one embodiment, the pressure area P3 may reflect the pressure in the eye under the conjunctiva. In such cases, pressure area P3 reflects a pressure that can be correlated with atmospheric pressure. Pressure area P3 may also reflect the pressure of a dry portion 260 of the subconjunctival space, separate and apart from the drainage site 250. Regardless of location, pressure area P3 is intended to reflect the reference atmospheric pressure in the vicinity of the eye or at the eye's surface, and when P3 or atmospheric pressure is used herein, it is intended to refer to atmospheric pressure as well as pressure that can be correlated with atmospheric pressure.

Generally, IOP is a gauge pressure reading—the difference between the absolute pressure in the eye (as reflected by P1) and atmospheric pressure (as reflected by P3). Atmospheric pressure, typically about 760 mm Hg, often varies in magnitude by 10 mmHg or more depending on weather conditions or indoor climate control systems. In addition, the effective atmospheric pressure can vary significantly—in excess of 100 mmHg—if a patient goes swimming, hiking, riding in an airplane, etc. Such a variation in atmospheric pressure is significant since IOP is typically in the range of about 15 mm Hg. Because the pressure area P3 reflects atmospheric pressure, the difference in pressure between the pressure areas P1 and P3 provides an indication of IOP (the pressure differential between the anterior chamber 240 and the atmospheric pressure). Thus, for accurate control of IOP, it is desirable to have an IOP control system reactive to the pressure differential across the pressure of the anterior chamber (as reflected by P1) and atmospheric pressure in the vicinity of the eye (as reflected by P3). Therefore, in one embodiment of the present disclosure, the IOP control system 200 reacts to the pressure differential across P1 and P3 continuously or nearly continuously so that the actual IOP (as P1-P3 or P1-f(P3)) can be responded to accordingly, where f(P3) indicates some function of P3.

The valve system 220 is connected to the drainage tube 210 and controls the flow of aqueous humor through the lumen 215 of the tube 210 from the anterior chamber 240 to the drainage site 250. The valve system 220 is disposed along, and may form a part of, the drainage tube 210 between the end 270 in the anterior chamber 240 and end 280 at the drainage site 250. In some embodiments, the valve system 220 is disposed within the lumen 215 of the drainage tube 210 between the end 270 and the end 280. The valve system 220 is configured to control the flow of fluid through the drainage tube 210, and thereby control pressure in the eye, including the IOP. For example, when the IOP is high, the valve system 220 may operate to permit increased flow through the drainage tube 210, and when IOP is low, the valve system 220 may operate to decrease the flow through the drainage tube 210. In the embodiment pictured in FIG. 2, the valve system 220 is configured to be continuously responsive to various pressure differentials (P1-P3 or P2-P3) and control fluid flow to the drainage site 250.

The valve system 220 includes as least one pressure-driven membrane valve 300 that does not require external power or feedback from electronic pressure sensors to operate. The valve 300 is configured to allow or block aqueous humor flowing from the anterior chamber 240 through the drainage tube 210 to any subsequent valves within the valve system 220 or to the drainage site 250. In the embodiment shown in FIG. 3, the pressure-driven membrane valve 300 includes a housing 310, a reference chamber 320, a valve seat 330, a fluid flow channel 335, a flow control membrane 340, and a boss member 350. In the pictured embodiment, the components of the valve 300 are generally circular in geometry and are symmetric about the center line AA. In alternative embodiments, different geometries for the valve are contemplated, including ovoid and rectangular geometries, for example.

The housing 310 is defined by a housing section 360 and a housing section 370, which mate with one another to form an enclosure within which various other components of the valve 300, such as the flow control membrane 340, the valve seat 330, and the boss member 350, are positioned. The housing section 370 includes a fluid inlet 380, a fluid outlet 390, and the valve seat 330. The valve seat 330 is positioned between the fluid inlet 380 and the fluid outlet 390 such that fluid flows from the fluid inlet 380, through the fluid flow channel 335, and to the fluid outlet 390. In alternative embodiments, the housing 310 may be integrally formed of the two sections 360, 370. In alternative embodiments, the housing sections 360, 370 may cooperate to form the fluid inlet 380 and the fluid outlet 390. The housing 310 may be constructed of any suitable biocompatible material, provided the material is able to maintain constructional integrity at high internal pressures and withstand pressure changes.

The reference chamber 320 is bounded and defined by at least the housing section 360 and the flow control membrane 340. The reference chamber 320 is in communication with pressure area P3, which is expected to reflect the atmospheric pressure. In some embodiments, the reference chamber 320 is in communication with the dry subconjunctiva. In alternative embodiments, the reference chamber 320 interfaces with another portion of the eye or to atmospheric pressure directly. Moreover, in alternative embodiments, a plurality of membranes using separate reference chambers (and reference chamber pressures) is contemplated for use in the valve 300.

In some embodiments, the valve seat 330 may be a floor surface of the housing section 370 while in other embodiments, the valve seat 330 may be the top of a structure, such as a boss. In the pictured embodiment, the boss member 350 forms the valve seat and is positioned to concentrically overlie the fluid inlet 380. It should be noted that some contemplated embodiments do not include the boss member 350. In a valve without a boss member, the central aperture of the valve seat 330 serves as the entrance to the fluid flow channel 335. In a valve without a boss member, the valve seat is shaped and configured such that when the flow control membrane 340 rests on the valve seat 330, the valve 300 is in a closed condition.

Figure 3:
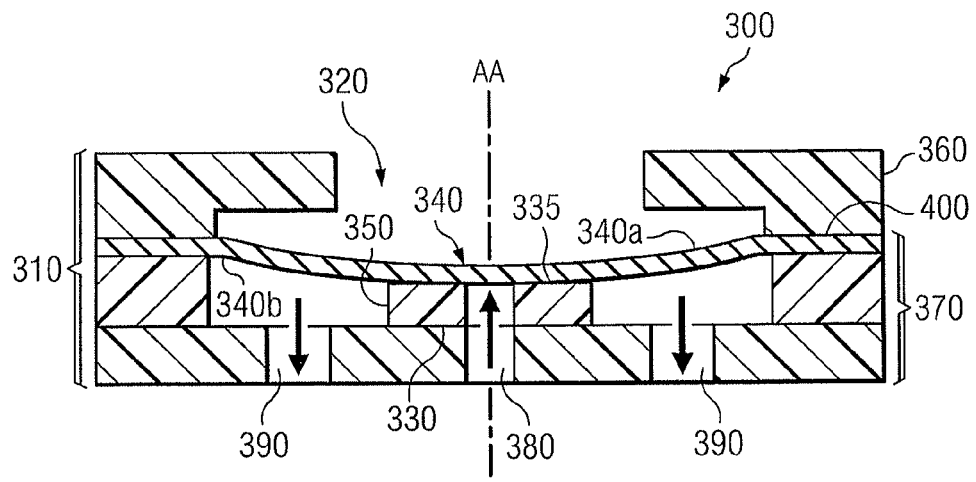
FIG. 3 is a schematic cross-sectional diagram of an exemplary pressure-driven valve in a closed condition according to one embodiment of the present disclosure.

In the pictured embodiment in FIG. 3, the boss member 350 is shaped as a generally annular or toroid component. The boss member 350 is shaped and configured such that when the flow control membrane 340 rests on the boss member 350, the valve 300 is in a closed condition, as shown in FIG. 3. The boss member 350 is positioned such that the central aperture of the boss member 350 and the fluid inlet 380 are co-aligned about the central axis AA. Accordingly, the boss member forms the valve seat at a raised position within the housing 300. Thus, in the embodiment pictured in FIG. 3, the central aperture of the boss member 350 serves as both the exit of the fluid inlet 380 and the entrance to the fluid flow channel 335, and when the flow control member 340 rests on the boss member 350, the valve 300 is in a closed position. The boss member 350 permits increased design flexibility and flow control for the valve 300. Varying the height and other dimensions of the boss member 350 affects the amount and rate of fluid flow through the valve 300.

In various embodiments, the boss member 350 may be configured as an integral extension of the housing section 370, or may be a separate component, and may be constructed (e.g., molded, machined, or built using Micro-Electro-Mechanical Systems (MEMS) microfabrication techniques) at the same time as the housing section 370. For example, the boss member may be fabricated by micromachining or MEMS techniques at the same time, or in processing steps before or after the fabrication of the housing section 370, depending on the exact nature of the fabrication process used (such as whether the process steps used for these features are primarily additive or subtractive in nature).

The fluid flow channel 335 comprises the circumferential gap that arises between the valve seat 330 and the flow control membrane 340 when the flow control member 340 deflects away from the valve seat 330 toward the reference chamber 320. As shown in FIG. 3, the fluid flow channel 335 can in some areas be restricted to zero or near-zero size in some dimension (in height, as drawn in FIG. 3) when the flow control membrane 340 rests on the valve seat 330 of the boss member 350 and the valve 300 is in a closed condition. In embodiments lacking a boss member, the fluid flow channel 335 can in some areas be restricted to zero or near-zero size in some dimension (e.g., height) when the flow control membrane 340 rests on the valve seat 330 on the floor of the housing section 370 and the valve 300 is in a closed condition.

Figure 4:
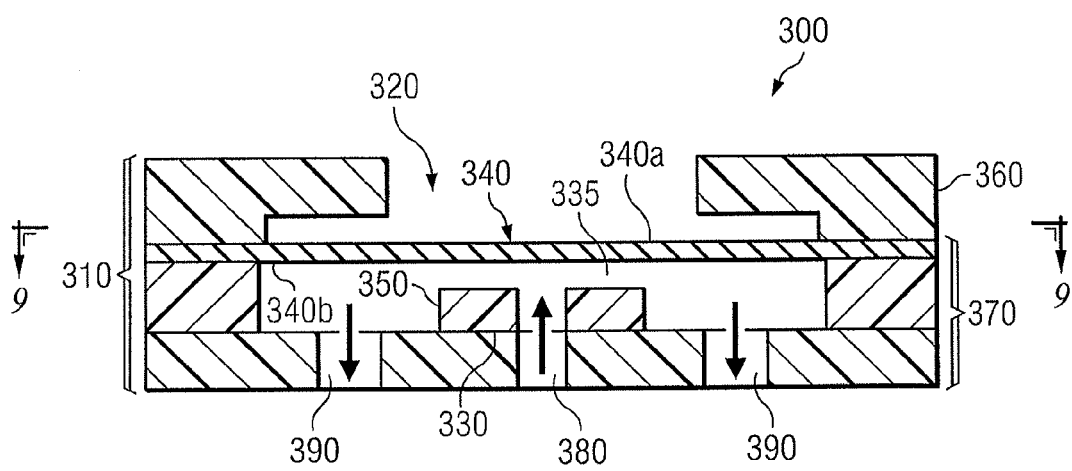
FIG. 4 is a schematic cross-sectional diagram of the pressure-driven valve shown in FIG. 3 in an open condition according to one embodiment of the present disclosure.

As shown in FIG. 4, however, the fluid flow channel 335 is not restricted or is less restricted when the flow control membrane deflects off the boss member 350 into the reference chamber 320 and the valve 300 is in an open condition. When the valve 300 is in an open condition, the fluid flow channel 335 is generally a constant height around the annular sealing surface of the boss member 350 (i.e., the gap between the boss member 350 and the membrane 340 is generally uniform) at any given time.

The flow control membrane 340 comprises a flexible, deformable, fluid-tight membrane or diaphragm that provides valve functionality by deflecting in response to pressure differentials across its two opposing sides. The flow control membrane 340 includes two substantially parallel sides, a side 340a and an opposite side 340b. The side 340a faces the reference chamber 320, and consequently conveys the pressure of pressure area P3. The side 340b is in fluidic communication with the lumen 215 of the drainage tube 210, and in particular the fluid inlet 380, and consequently conveys the pressure of pressure area P1. The side 340b of the flow control membrane 340 is configured to selectively seal against the boss member 350 and thereby close the valve 300 when the pressure against the side 340a sufficiently outweighs the pressure against the side 340b. As will be explained in further detail below, the flow control member 340 deflects in response to pressure differences between the fluid inlet 380 and the reference chamber 320 to at least partially open and close the valve 300 by changing the dimensions of the fluid flow channel 335.

As shown in FIG. 3, the flow control membrane 340 is securely held in place within the housing 310 so that it will not be displaced by the force of the fluid flowing through the valve 300. The valve 300 may be in the closed configuration, as shown in FIG. 3, in a scenario where the pressure difference between the pressures in the fluid in the drainage tube 210 (P1) and the reference chamber 320 (P3) is generally lower than a target value—for example, 6 mm Hg (corresponding the lowest safest IOP level). Conversely, the valve 300 may be in the open configuration, as shown in FIG. 4, in a scenario where the pressure difference between the pressure in the fluid in the drainage tube 210 (P1) and the reference chamber 320 (P3) is generally higher than a target value—for example, 12 mm Hg+/−1 mm Hg (corresponding to the highest IOP acceptable prior to allowing drainage).

In the embodiment pictured in FIG. 3, the flow control membrane 340 is anchored between the housing section 360 and the housing section 370. More specifically, a peripheral zone 400 of the flow control membrane 340 is sandwiched between the walls of the housing section 360 and the walls of the housing section 370. The housing section 360, the membrane 340, and the housing section 370 are secured into this arrangement by any of a variety of known methods, including by way of non-limiting example, adhesive, welding, mechanical fasteners, or adhesion techniques associated with MEMS microfabrication. Regardless of how the membrane 340 is secured within the housing 300, at least a portion of the housing 300 applies a compressive force to a periphery of the membrane 340 to maintain it in a desired position relative to the valve seat 330 or boss member 350.

Figure 5:
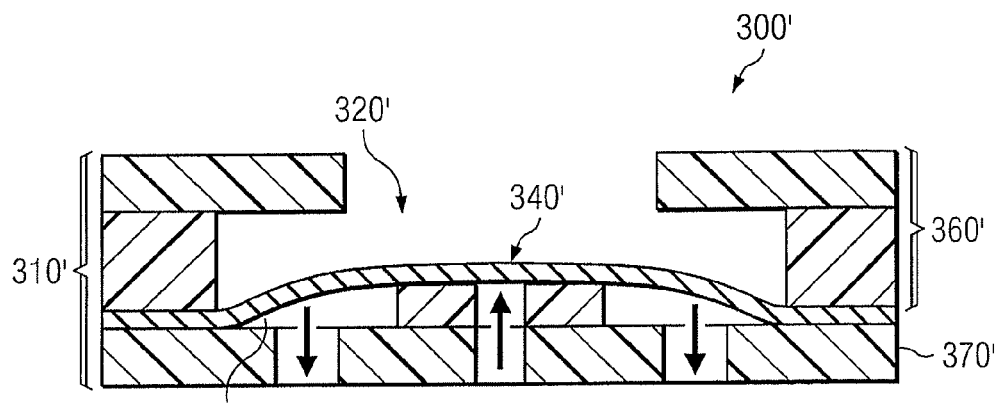
FIG. 5 is a schematic cross-sectional diagram of another exemplary pressure-driven valve in a closed condition according to one embodiment of the present disclosure.

As illustrated in one embodiment shown in FIG. 5, the membrane 340 and the other features of the valve can be designed with a pre-biased condition such that the valve 300 is normally closed (for instance when P1-P3 is at or near zero or some other desired value) and its biased condition is such that the above mentioned open and closed pressure requirements are met. Such biasing can be achieved by any of a variety of techniques. For example, in some embodiments, biasing may be achieved by sizing and configuring valve features that sandwich the membrane (e.g., the housing sections 360 and 370) to vary the vertical position of the peripheral zone 400 of the flow control membrane 340. In some embodiments, biasing may be achieved by pre-shaping the membrane 340 during manufacturing to have a pre-determined shape a stepped membrane shape (such as corrugations) in which the center of the membrane resides lower than the peripheral edges.

The valve 300 is configured as a flow control valve that can completely or partially block the flow of aqueous humor by deflecting the flow control membrane 340 completely or partially across the fluid inlet 380 and/or the fluid flow channel 335. The housing 310 is configured to connect with drainage tube 210 such that deflection of the flow control membrane 340 at least partially opens and closes the lumen 215 to the outflow of aqueous humor. As described above, the position of the flow control member 340 determines whether the valve 300 is in an open, partially open, or closed condition. When the membrane 340 seals against the boss member 350, the valve 300 is in a closed condition. When the membrane 340 deflects away from the boss member 350, the valve 300 is in an open or partially open condition.

The valve 300 is in fluidic communication with the drainage tube 210 and in communication with the dry subconjunctiva. In particular, the fluid inlet 380 fluidically interfaces with the drainage tube 210 (reflecting pressure area P1). The reference chamber 320 interfaces with the dry subconjunctiva (reflecting pressure area P3). The flow control membrane 340 extends across the housing 310 to form a sealed separation between the reference chamber 320 and the fluid inlet 380, thereby creating an effective separation between pressure areas P3 and P1, respectively. Accordingly, as the pressure increases against one side of the flow control membrane 340, the pressure increase acts to displace the flow control membrane 340 in the direction away from the higher pressure. The fluid inlet 380 conveys the pressure of pressure area P1 on one side 340b of the flow control membrane 340. The reference chamber 320 conveys the pressure of pressure area P3 on the opposite side 340a of the flow control membrane 340.

As mentioned above, the flow control membrane 340 directs flow by deflecting within the housing 310 of the valve 300 in response to the pressure differential between the fluid chamber pressure (as reflected by pressure area P1) against one side 340b of the flow control membrane 340 and the dry subconjunctival pressure (as reflected by pressure area P3, which is expected to correspond to atmospheric pressure) against the opposite side 340a of the flow control membrane 340. The cracking pressure of the valve 300 is the pressure threshold above the pressure of the reference chamber 320 (P3) at which the membrane 340 deflects off the boss member 350. In particular, if the IOP exceeds the cracking pressure of the flow control membrane 340, then the valve 300 will assume an open condition and allow free flow to regulate the IOP down to the desirable range. Otherwise, the valve 300 remains in a closed condition because the IOP (P1-P3) or pressure difference across the membrane 340 is below the cracking pressure.

The cracking pressure is dependent on the type, size, and stiffness of the flow control membrane 340 and the structure of the valve housing 310. Accordingly, the cracking pressure may be preselected by controlling these parameters during manufacturing or assembly processes.

The size of the opposing sides 340a, 340b of the flow control membrane 340 is another factor affecting the pressure differential required to overcome the cracking pressure and open the valve 300. Given that Force=Pressure×Area, for an unchanged area over which the membrane side 340a is exposed to the reference pressure P3, comparatively reducing the area of the membrane side 340b, which is exposed to the fluid pressure of inlet 380 (P1), serves to reduce the lift force component (upward in FIGS. 3-5) on the membrane 340 associated with the membrane side 340b. In one embodiment, this is achieved by increasing the width of the boss member 350 into the space of the inlet 380. For example, for a given valve 300 in the closed configuration, the opening (cracking) pressure of the membrane 340 can be increased by decreasing the area of the inlet 380 exposed to membrane side 340b.

In one example, these dimensions are selected so that the valve 300 remains closed when the IOP (P1-P3) is below the desired cracking pressure. After implantation of the valve 300, the patient's IOP will begin to approximate the cracking pressure of the valve 300. Therefore, the surgeon may select a valve 300 having a particular cracking pressure based on the most appropriate or desired IOP range for the treatment of a particular condition.

FIG. 3 illustrates the valve 300 in a closed, flow-blocking position. In the situation depicted in FIG. 3, the valve 300 is in a closed position because the IOP (P1-P3) is not in excess of the cracking pressure of the valve 300, and the pressure of the reference chamber 320 forces the membrane 340 against the boss member 350. The flow control membrane 340 is resting on the sealing surface of the boss member 350, thereby blocking the flow of aqueous humor from the fluid inlet 380 to the fluid outlet 390 and through the drainage tube 210. It is desirable not to allow the IOP to drop below a certain threshold, for example, 6 mmHg. Any intraocular pressure below such a threshold is considered hypotonous pressure and is dangerous to the eye, as explained above. The valve system 220 is self-limiting because the pressure-driven valve 300 will not open unless the pressure differential across the valve 300 overcomes the cracking pressure of the valve. Accordingly, if the IOP (P1-P3) is lower than the cracking pressure of the flow control membrane 340, then the valve 300 will not open and aqueous humor will not leave the anterior chamber 240 through the IOP control system 200.

FIG. 4 illustrates the valve 300 in an open, flow-permitting condition. When the IOP (P1-P3) is in excess of the cracking pressure of the valve 300 (equivalent to the target IOP), the membrane 340 rises off the boss member 350 and the valve 300 opens, thereby allowing aqueous humor to flow through the drainage tube 210 from the fluid inlet 380 to the fluid outlet 390 in the direction of possible additional flow regulating valves and the drainage site 250. Accordingly, the valve 300 is in an open condition because the IOP (P1-P3) is in excess of the cracking pressure of the flow control membrane 340 (equivalent to the target IOP), for example 12 mm Hg+/−1 mm Hg. The flow control membrane 340 allows flow through the tube 210 by deflecting off the boss member 350 and into the reference chamber 320 in response to the pressure differential between the anterior chamber pressure (as reflected by pressure area P1 in the fluid inlet 380) against one side 340b of the flow control membrane 340 and the dry subconjunctival pressure (as reflected by pressure area P3 in the reference chamber 320) against the opposite side 340a of the flow control membrane 340. Because the valve 300 is in an open condition, the aqueous humor can flow through the drainage tube 210 from the fluid inlet 380 to the fluid outlet 390 in the direction of any remaining flow control devices (including, without limitation, valves, pumps, and/or other flow-regulating devices) and the drainage site 250. This ensures that drainage of the aqueous humor can occur through the drainage tube 210 if the IOP is elevated. In alternate embodiments, the valve 300 may have any number of fluid inlets 380 and fluid outlets 390.

The resistance to flow of the flow control member 340 decreases with greater displacement. Accordingly, in higher pressure situations, the valve 300 will assume a more open condition than in lower pressure situations. The higher the pressure of the fluid within the fluid inlet 380 (P1) in comparison with the pressure of the reference chamber 320 (P3), the more the flow control member 340 deforms, thereby enlarging the entrance to and the dimensions of the fluid flow channel 335 and allowing greater amounts of aqueous humor to flow from the fluid inlet 380, across the valve seat 330, and through the fluid outlet 390. Conversely, the lower the pressure of the fluid within the fluid inlet 380 (P1) in comparison with the pressure of the reference chamber 320 (P3), the more the flow control membrane 340 deforms to block the entrance to the fluid flow channel 335 and possibly to reduce the dimensions available for flow within the fluid flow channel 335, thereby in one or both ways restricting aqueous humor from entering the fluid flow channel 335. That is, the flow resistance can be realized by two possible mechanisms: reducing the size of the fluid inlet 380 and reducing the dimensions of the flow channel 335. Decreasing size of the fluid inlet 380 allows a pressure drop because of a nozzling effect (a portion of pressure drop occurs even within inviscid flow theory). Reducing the channel height of flow channel 335 can provide significant resistance for the length of flow channel 335 because of viscous losses.

FIG. 5 shows a valve 300', which is similar to the valve 300 except for the differences noted herein. The individual components of the valve 300', including a flow control membrane 340', a boss member 350', a housing section 360', and a housing section 370', are similar to the corresponding components of the valve 300. In the embodiment pictured in FIG. 5, the flow control membrane 340' is anchored between the housing section 360' and the housing section 370', which are shaped and configured such that the center of the flow control membrane 340' is slightly deformed about the boss member 350' when the valve 300' is at rest or at a neutral condition. A valve having this configuration may be utilized in a scenario where the pressure in the reference chamber 320' (P3) is generally lower than the pressure in the fluid in the drainage tube 210 (P1).

Figure 6A:
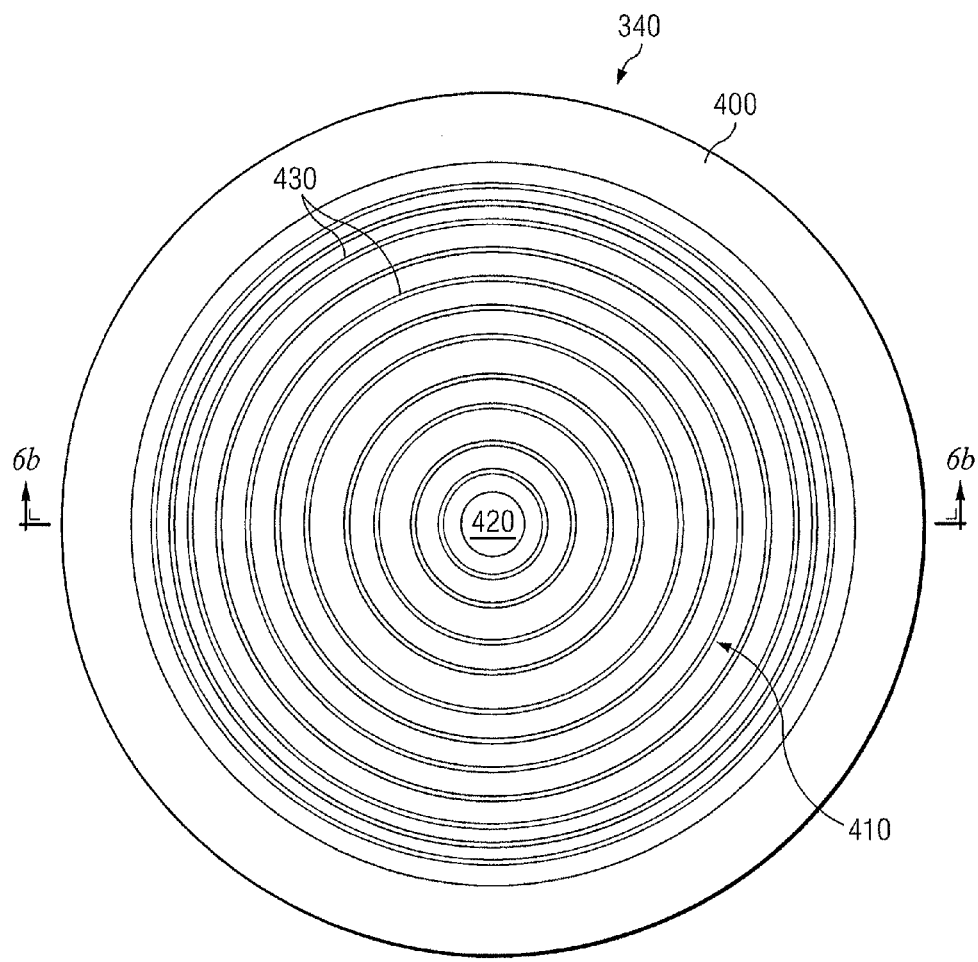
FIG. 6a is a top plan view of an exemplary flow control membrane useable in a pressure-driven valve according to one embodiment of the present disclosure.

FIG. 6a illustrates a top plan view of the surface of the flow control membrane 340 according to one embodiment of the present disclosure. In the pictured embodiment, the flow control membrane 340 is shaped and configured as a corrugated, substantially planar membrane having a circular shape. Other shapes are also contemplated for the membrane 340, including, but not by way of limitation, rectangular or ovoid shapes. The shape of the flow control membrane 340 may be chosen depending upon spatial, pressure drop, material, and flow rate constraints. The flow control membrane 340 is shaped and configured to define a peripheral zone 400, a corrugated zone 410, and a central zone 420. The corrugated zone 410, which surrounds the central zone 420 and is bounded by the peripheral zone 400, includes a plurality of concentric corrugations 430. Alternative embodiments may include any number of corrugations. For example, some embodiments may include one corrugation. As mentioned above, the peripheral zone 400 of the flow control membrane 340 is sandwiched between the walls of the housing section 360 and the walls of the housing section 370 such that the membrane 340 is anchored within the housing 310.

Figure 6B:
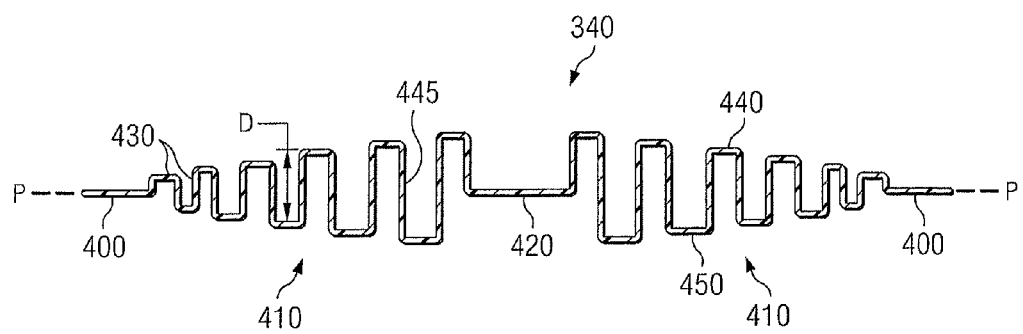
FIG. 6b is a cross-sectional view of the flow control membrane of FIG. 6a according to one embodiment of the present disclosure.

FIG. 6b depicts a cross-sectional view taken along lines 6b-6b in FIG. 6a, showing the corrugations within the flow control membrane 340. As shown in FIG. 6b, the peripheral zone 400 may be disposed in substantially the same plane P as the central zone 420 when the membrane 340 is at rest and unstressed (and not positioned to deform over a boss member 350 as in FIG. 5). In alternate embodiments, the peripheral zone is disposed in a different plane than the central zone when the membrane is at rest and unstressed. The corrugations 430 include alternating peaks (or ridges) and valleys (or grooves) connected by sidewalls within the membrane 340. Each corrugation includes a peak 440 connected by a sidewall 445 to a neighboring valley 450 and another sidewall 445. The plurality of corrugations 430 may be arranged in a periodic configuration. In particular, each corrugation extends downwards from a peak 440 along a sidewall 445 to a neighboring valley 450 and extends upwards from the valley 450 along an adjacent sidewall 445 to a neighboring peak 450 to complete the periodic configuration of the corrugation.

In FIG. 6b, the corrugations 430 are shaped to include rectangular or squared off edges. Various other embodiments may include edges of any of a variety of shapes, including, by way of non-limiting example, rounded and trapezoidal, such as acutely or obtusely angled edges.

The corrugated membrane is not limited to a particular number or arrangement of corrugations (or corrugation zones). As shown in FIG. 6b, the membrane 340 may include corrugations of varying amplitudes or depths D, which reflect the vertical distance between neighboring peaks and valleys. The depths D of the corrugations are not limited to any particular depth. In the embodiment shown in FIG. 6b, the corrugations 430 closer to the central zone 420 are of greater amplitude and depth D than those corrugations 430 closer to the peripheral zone 400. In other embodiments, the corrugations 430 could be of the same peak 440-to-valley 450 depth D throughout the corrugated zone 410. In yet other embodiments, the corrugations 430 closer to the central zone 420 may be of lower depths D than those corrugations 430 closer to the peripheral zone 400. In some embodiments, the membrane may include various corrugated zones, each having corrugations of a particular depth. The depths, shape, arrangement and combination of corrugations may be optimized to provide a particular physical deflection profile as a function of pressure differentials across the membrane.

When the flow control membrane 340 is operative in a valve 300, any pressure differential to which the membrane 340 is exposed will cause the membrane 340 to deflect or displace in one direction or the other, with the greatest axial displacement occurring at the central zone 420. Deflection of the membrane 340 is generally radially symmetric about the central zone 420. The corrugations 430 aid in membrane flexibility, giving the capability of a larger membrane response (deflection) in response to a given input pressure differential. The characteristics and placement of the corrugations 430 can affect both the amount and type of deflection of the membrane 340 at a given pressure.

The corrugated flow control membrane 340 may be unitarily made or formed by stamping, molding, or any other suitable means known in the art from any suitable biocompatible, flexible material. The membrane 340 can be constructed of any suitable biocompatible material that can move, flex, deform, or deflect in response to differential pressures. The material may comprise a thermoplastic material, an elastomeric material, a thermoplastic elastomer, materials such as those used in semiconductor and MEMS processing such as Silicon or Silicon Nitride, or any biocompatible metals such as gold, or any combinations of the foregoing. In some embodiments, the flow control membrane 340 is constructed using the techniques common to fabricate a MEMS membrane, such as, but not by way of limitation, a Parylene membrane. Parylene is a biocompatible, inert, and nonbiodegradable material that is used to fabricate mechanically robust microstructures. MEMS membranes are easier to deflect (i.e., they have a larger throw at a lower pressure) when designed and fabricated using increasingly compliant materials, increasingly thin membranes, and/or increasingly large radii or lengths. In addition to being actuatable by pressure differentials across the membrane, MEMS membranes may also be actuated by several other means, including, but not by way of limitation, electrostatically, magnetically, and thermally.

For purposes of practicality, the flow control membrane 340 should be thick enough to be durable and resistant to corrosion and leakage. However, the membrane 340 should also be thin enough to provide the necessary flexibility and deflection capabilities which are required in a substantially planar membrane designed for use in a pressure-responsive IOP control system 200. The optimum membrane thickness depends on the material chosen (including its stiffness/elasticity and its ability to withstand cycling through the desired deflection over time), the desired membrane deflection, the pressure differentials of the particular application, and the arrangement/presence of corrugations. For example, for a Parylene membrane, the membrane thickness may range from 1 μm-25 μm. For a Silicon membrane, the membrane may range in thickness from 0.5 μm -10 μm. For metallic membranes made of relatively elastic materials, an intermediate range of membrane thicknesses of 0.5 μm-5 μm may be utilized. This list of membrane materials and thickness ranges is not intended to be limiting. Where suitable, other materials and combinations of materials with suitably adjusted thicknesses may be advantageous, and thicknesses outside of these ranges may be advantageous for specific instances of system design and application. Membrane thickness, material, and diameter, in combination with the number, placement, and depth of the corrugations, all affect the cracking pressure of the flow control membrane 340. It should be noted that some contemplated embodiments do not include the corrugations 430.

To ensure biocompatibility, the valve 300 can be coated or encapsulated in a biocompatible material including, but not by way of limitation, polypropylene, silicone, parylene, or other known biocompatible materials.

Figure 7:
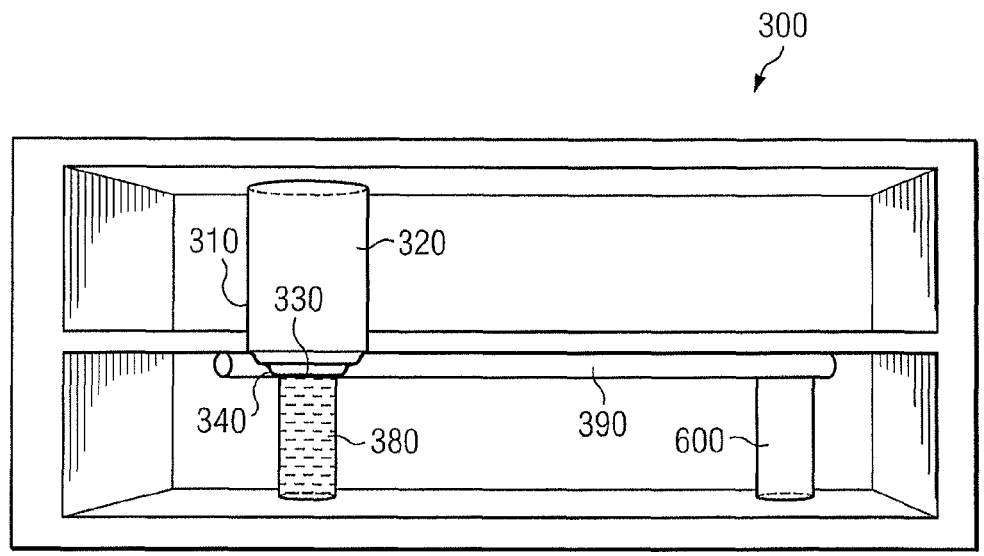
FIG. 7 is an illustration of a partially transparent 3D view of a pressure-driven valve in the closed condition according to one embodiment of the present disclosure.
Figure 8:
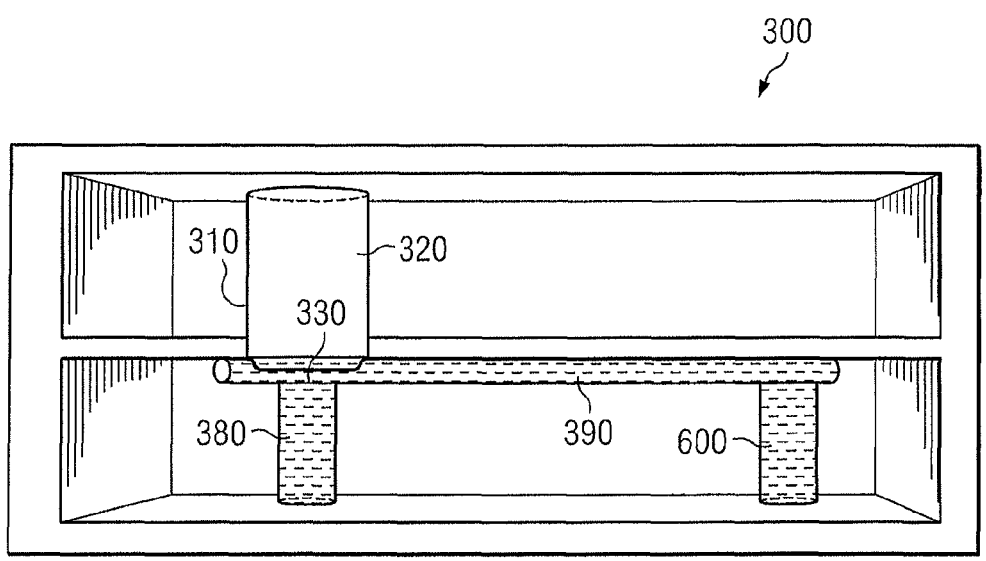
FIG. 8 is an illustration of a partially transparent 3D view of the pressure-driven valve of FIG. 7 in an open condition according to one embodiment of the present disclosure.

FIGS. 7 and 8 present three dimensional, transparent side views of the valve 300 according to one embodiment of the present disclosure. In FIGS. 7 and 8, the housing 310 is shown in its larger environment including a fluid inlet 380, a fluid outlet 390, a flow control membrane 340, and a connection passage 600. The connection passage 600 fluidly connects the drainage tube 210 (not shown) to the fluid outlet 390.

FIG. 7 illustrates the valve 300 in a closed condition, wherein the flow control membrane 340 is deflected towards the valve seat 330 to seal the fluid outlet 390, thereby preventing the flow of fluid the fluid inlet 380 into the fluid outlet 390.

FIG. 8 illustrates the valve 300 in an open condition, wherein the flow control membrane 340 (not shown here) is deflected away from the valve seat 330 toward the reference chamber 320, thereby allowing the flow of fluid from the fluid inlet 380 into the fluid outlet 390.

Figure 9:
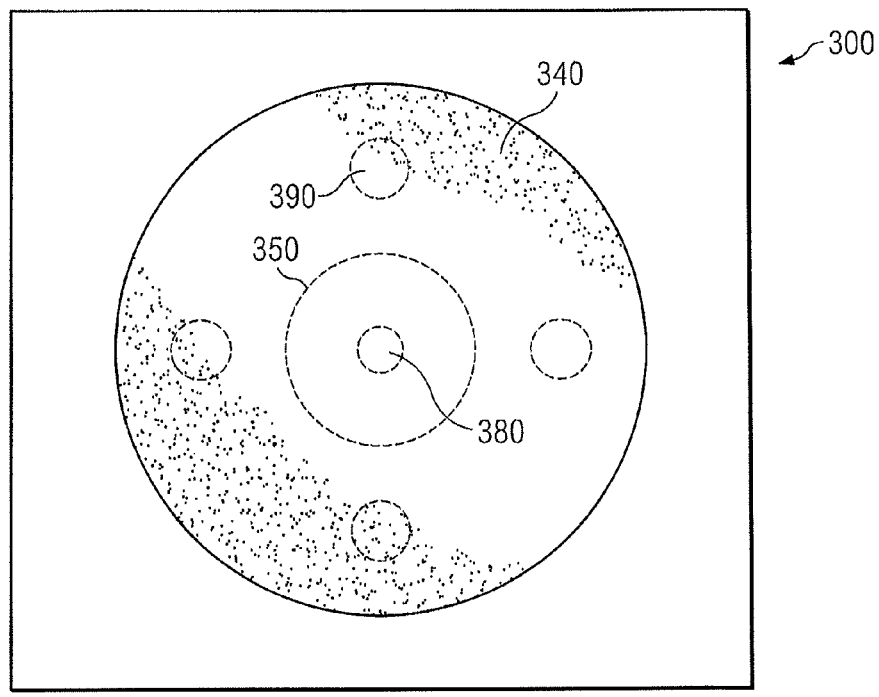
FIG. 9 is a schematic showing a top plan view of a pressure-driven valve according to one embodiment of the present disclosure.
Figure 10:
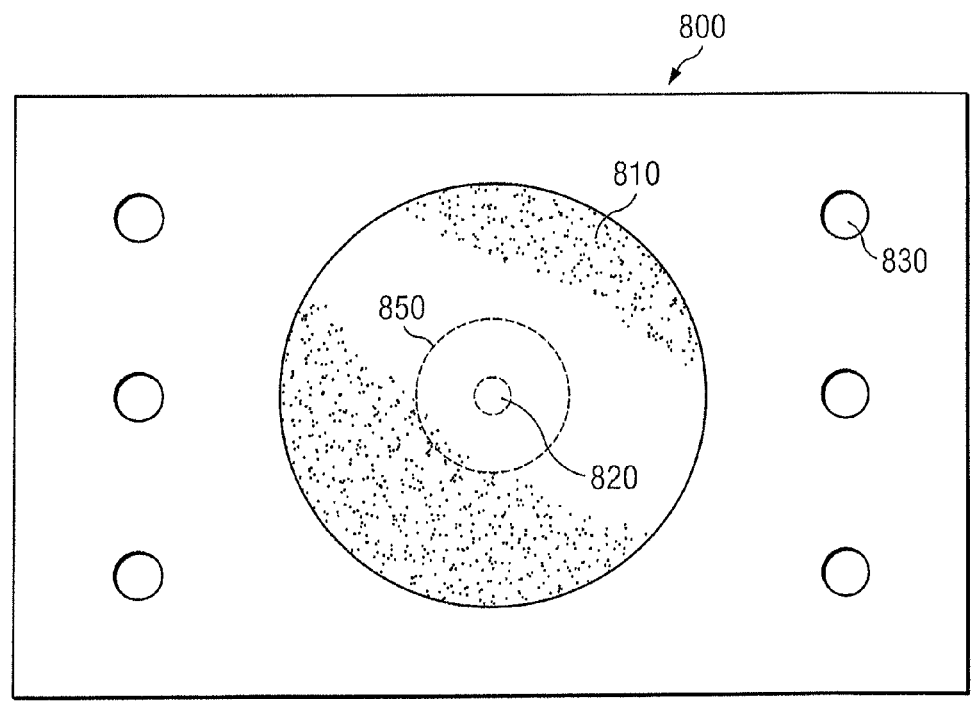
FIG. 10 is a schematic showing a top plan view of a pressure-driven valve according to one embodiment of the present disclosure.

FIGS. 9 and 10 are schematic illustrations of top plan views of two different embodiments of the pressure-driven membrane valve according to the present disclosure. FIG. 9 depicts a cross-section through lines 9-9 in FIG. 4 showing the valve 300 including the circular flow control membrane 340, the fluid inlet 380, four fluid outlets 390, and the boss member 350. The fluid inlet 380 is positioned centrally aligned with and under the membrane 340. The fluid outlets 390 are positioned under the membrane 340 as well.

FIG. 10 depicts a valve 800 including a circular flow control membrane 810, a fluid inlet 820, six fluid outlets 830, and a boss member 850. The flow control membrane 810 may be configured as part of the lower or upper housing section. The valve may have a circular geometry as shown, or may have varying geometry, such as, by way of non-limiting example, rectangular, ovoid, or oblong geometry. As noted above, the membrane need not be circular, and could be square or rectangular or other advantageous shapes. Moreover, the valve is not limited to any particular arrangement or number of fluid inlets and fluid outlets. As shown in FIG. 10, the fluid inlet 820 is positioned to be centrally aligned with and under the membrane 810. The fluid outlets 830 are positioned a distance apart from the membrane 810. In other embodiments, the inlet and/or the outlet may be positioned outside of the area of the membrane, making it possible for the fluid outlets to be positioned further from the fluid inlet than shown in FIGS. 9 and 10.

Though the pressure-driven valves 300, 300' are depicted as comprising a disk-like flow control membrane and a boss member in FIGS. 3-5, the valves 300, 300' may be comprised of any of a number of different flow control elements that meter, restrict, or permit the flow of aqueous humor from the anterior chamber 240 to the drainage site 250. For example, trapped gaseous medium can be used in conjunction with a compliant membrane to enable the pressure-driven valves. In some embodiments, the flow control membrane 340 of the valve 300 may be in contact with a biocompatible gel to transmit pressure from the aqueous humor at a region of interest. The biocompatible gel may be one of a variety of biocompatible gels, including silicone dielectric gels used with medical grade piezoresistive pressure sensors. These modifications prevent the formation of solid fibers as a result of the proteinaceous content of the aqueous humor, which could mechanically disrupt valve operation. In some embodiments, the flow control membrane 340 may be used in conjunction with and/or actuate a pump. In addition, the valve 300 may be positioned anywhere in fluid communication with the drainage tube 210, whether within or along the drainage tube 210.

Conventional passive check valves in drainage device implants (e.g., the Ahmed Valve) provide a reduced risk of hypotony in the weeks immediately following surgery. But these conventional valves have no mechanism for accounting for drainage site or bleb pressure. The systems disclosed herein may adjust to control flow to the bleb. Accordingly, the systems and methods disclosed herein provide a device that a) requires zero to minimal power (internal or external), and b) presents a mechanism of minimizing bleb height (reducing or eliminating bleb) by controlling the flow through the IOP control system 200 based on pressure differentials, which could significantly reduce the effect of fibrosis and also reduce or eliminate other issues related to bleb management.

The devices, systems, and methods described herein achieve IOP control with a very small device that utilizes zero to very low power. In some embodiments, the device may require no external power to regulate pressure and/or flow within a desired range. In some embodiments, the device may require no external power to regulate pressure and/or flow within a desired range for a certain amount of time as part of a system that includes elements that are powered for a certain length of time. The system takes into account drainage or bleb pressure in regulating drainage flow. Accordingly, based on pressure-driven valves to control the flow rate of aqueous humor, the system provides suitable care for a patient suffering from irregular intraocular pressure.

Embodiments in accordance with the present disclosure may be used in a variety of applications to regulate flow and/or pressure. For example, but not by way of limitation, embodiments of the present disclosure may be utilized to regulate flow and/or pressure as part of a microanalytical system, a dialysis system, a process control system, a drug delivery system, a solar thermal system, a cooling system, and/or a heating system. Some embodiments of the present disclosure may be utilized to regulate pressure and/or flow in a variety of fluidic systems such as, but not by way of limitation, the urinary tract, the brain (e.g., to regulate intracranial pressure), and the circulatory/renal system (e.g., as part of a dialysis system). Moreover, some embodiments are shaped and configured for implantation in a patient, while others are not.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

I claim:

1. A control valve for a fluidic system, comprising:
a housing including a fluid inlet and a fluid outlet;
a boss member on a portion of the housing, the boss member providing a valve seat; and
a flow control membrane anchored within the housing to form a reference chamber on a first side of the flow control membrane and a fluid flow channel, configured to convey aqueous humor from an anterior chamber of the eye, on a second opposing side of the membrane, the reference chamber having an opening to couple the reference chamber to a varying pressure such that the reference chamber provides a varying reference chamber pressure, the fluid flow channel selectively opening and closing to permit fluid to flow from the fluid inlet to the fluid outlet, the flow control membrane configured to control flow through the fluid flow channel from the fluid inlet to the fluid outlet by deflecting away from or toward the valve seat in response to pressure differentials of the varying reference chamber pressure and the fluid flow channel pressure acting on the opposing sides of the flow control membrane.

2. The control valve of claim 1, the housing further including a first housing section and a second housing section, wherein the flow control membrane is anchored between the first housing section and the second housing section.

3. The control valve of claim 1, wherein the fluid inlet comprises an opening through the boss member and the bottom portion of the housing, and wherein the housing comprises the boss member.

4. The control valve of claim 1, wherein the flow control membrane is anchored to the housing in a valve-closed position when the pressure differential is zero.

5. The control valve of claim 1, wherein the fluid flow channel comprises a gap between the valve seat and the flow control membrane.

6. The control valve of claim 1, wherein the flow control membrane comprises a flexible, fluid-tight membrane configured to deflect away from the valve seat in response to an elevated pressure.

7. The control valve of claim 6, wherein the flow control membrane comprises a circular membrane including at least one annular corrugation extending concentrically across the membrane.

8. The control valve of claim 7, wherein the flow control membrane includes a plurality of corrugations of varying shapes or arrangements.

9. The control valve of claim 1, wherein the flow control membrane is configured to control flow through the fluid flow channel by deflecting in response to pressure differentials between an anterior chamber of the eye and atmospheric pressure acting on the flow control membrane.

10. An IOP control system for implantation in an eye of a patient, comprising:
a drainage tube configured to convey aqueous humor from an anterior chamber of the eye; and a boss member on a portion of the housing, the boss member providing a valve seat;
a pressure-driven membrane valve in fluid communication with the drainage tube and with atmospheric pressure, the pressure-driven membrane valve actuatable in response to pressure differentials and configured to control flow rates of the aqueous humor along the drainage tube by deflecting away from or toward the valve seat in response to pressure differentials between the anterior chamber of the eye and the atmospheric pressure acting on the pressure-driven membrane valve.

11. The IOP control system of claim 10, wherein the pressure-driven membrane valve comprises:
a housing including a fluid inlet and a fluid outlet;
the valve seat positioned within the housing between the fluid inlet and the fluid outlet; and
a flow control membrane anchored within the housing to form a reference chamber on a first side of the flow control membrane and a fluid flow channel on a second side of the membrane, the fluid flow channel selectively opening and closing to permit fluid to flow from the fluid inlet to the fluid outlet, the flow control membrane configured to control flow through the fluid flow channel from the fluid inlet to the fluid outlet by deflecting in response to pressure differentials acting on the sides of the flow control membrane.

12. The IOP control system of claim 11, wherein the flow control membrane comprises:
a planar central zone;
a corrugated zone surrounding the planar central zone; and
a peripheral zone surrounding the corrugated zone.

13. The IOP control system of claim 11, the housing further including a first housing section and a second housing section, wherein the flow control membrane is anchored between the first housing section and the second housing section.

14. The IOP control system of claim 11, wherein the fluid flow channel comprises a gap between the valve seat and the flow control membrane.

15. The IOP control system of claim 11, further comprising a boss member adjacent the fluid inlet, the valve seat formed on the boss member.

16. The IOP control system of claim 11, wherein the flow control membrane comprises a flexible, fluid-tight membrane configured to deflect away from the boss member in response to an elevated IOP in the anterior chamber of the eye.

17. The IOP control system of claim 10, wherein the pressure-driven membrane valve comprises a circular flow control membrane including at least one corrugation extending concentrically across the membrane.

18. The IOP control system of claim 17, wherein the flow control membrane includes a plurality of corrugations of varying amplitudes and depths.

19. The IOP control system of claim 10, wherein the pressure-driven membrane valve and a second valve are arranged in series to operate independently of each other.

20. A pressure-driven IOP control valve for implantation in an eye of a patient, comprising:
a housing including a fluid inlet and a fluid outlet; and
a flow control membrane anchored within the housing to form a reference chamber on a first side of the flow control membrane and a fluid flow channel on a second side of the membrane, the fluid flow channel fluidly connecting the fluid inlet to the fluid outlet, a flow control membrane including a plurality of varying corrugations possessing varying shapes or arrangements, at least one corrugation extending up from and down below a planar central zone of the flow control membrane and configured to control flow through the fluid flow channel from the fluid inlet to the fluid outlet by deflecting in response to pressure differentials acting on the sides of the flow control membrane.

21. The pressure-driven IOP control valve of claim 20, wherein the plurality of corrugations extends concentrically across the flow control membrane.

22. The pressure-driven IOP control valve of claim 20, further comprising a valve seat positioned within the housing between the fluid inlet and the fluid outlet.

23. The pressure-driven IOP control valve of claim 20, wherein the fluid flow channel comprises an annular gap between the valve seat and the flow control membrane.

24. The pressure-driven IOP control valve of claim 23, wherein the flow control membrane closes the fluid flow channel by deflecting against the valve seat to block the fluid inlet in response to pressure differentials acting on the sides of the flow control membrane.

25. The pressure-driven IOP control valve of claim 20, wherein the flow control membrane is configured to control flow through the fluid flow channel by deflecting in response to pressure differentials between an anterior chamber of the eye and atmospheric pressure acting on the flow control membrane.

26. The pressure-driven IOP control valve of claim 20, further comprising a boss member, the valve seat formed on the boss member.

* * * * *